(12) United States Patent
Lin et al.

(10) Patent No.: US 12,208,115 B2
(45) Date of Patent: Jan. 28, 2025

(54) PH-RESPONSIVE HYDROGEL AND MANUFACTURING METHOD THEREOF

(71) Applicants: National Health Research Institutes, Zhunan Town (TW); National Taiwan University, Taipei (TW)

(72) Inventors: Feng-Huei Lin, Zhunan Town (TW); Rui-Chian Tang, Zhunan Town (TW); Tzu-Chien Chen, Taipei (TW)

(73) Assignees: NATIONAL HEALTH RESEARCH INSTITUTES, Miaoli County (TW); NATIONAL TAIWAN UNIVERSITY, Taipei (TW)

( * ) Notice: Subject to any disclaimer, the term of this patent is extended or adjusted under 35 U.S.C. 154(b) by 255 days.

(21) Appl. No.: 18/075,339

(22) Filed: Dec. 5, 2022

(65) Prior Publication Data

US 2024/0122965 A1 Apr. 18, 2024

(30) Foreign Application Priority Data

Oct. 17, 2022 (TW) .................................. 111139328

(51) Int. Cl.
| | | |
|---|---|---|
| *A61K 31/732* | (2006.01) | |
| *A61K 9/06* | (2006.01) | |
| *A61K 31/737* | (2006.01) | |
| *A61P 3/04* | (2006.01) | |

(52) U.S. Cl.
CPC .............. *A61K 31/732* (2013.01); *A61K 9/06* (2013.01); *A61K 31/737* (2013.01); *A61P 3/04* (2018.01)

(58) Field of Classification Search
CPC ...... A61K 31/732; A61K 9/06; A61K 31/737; A61P 3/04
See application file for complete search history.

(56) References Cited

PUBLICATIONS

Rui-Chian Tang et al., "Design Strategy for a Hydroxide-Triggered pH-Responsive Hydrogel as a Mucoadhesive Barrier to Prevent Metabolism Disorders," ACS Appl. Mater. Interfaces 2021, vol. 13, No. 49, 58340-58351, Dec. 6, 2021.

*Primary Examiner* — Robert A Wax
*Assistant Examiner* — Kimberly Barber
(74) *Attorney, Agent, or Firm* — Muncy, Geissler, Olds & Lowe, P.C.

(57) ABSTRACT

A pH-responsive hydrogel, which is synthesized by using mixed pectin and sucralfate treated with a small amount of acid to form a pH-responsive hydrogel. The pH-responsive hydrogel can form a temporary coating on the surface of the gastrointestinal tract to reduce excessive nutrient absorption, and exhibits excellent barrier properties and mucosal adhesion effects, which are useful for reducing blood sugar rise and weight gain, the liver fat accumulation, body fat accumulation and blood low-density lipoprotein that have a significant effect. In addition, the technical principles disclosed in the pH-responsive hydrogel should be applied to other polymer materials to manufacture different pH-responsive hydrogels.

15 Claims, 13 Drawing Sheets

PH-RESPONSIVE HYDROGEL AND MANUFACTURING METHOD THEREOF

BACKGROUND OF THE INVENTION

Field of the Invention

The present invention relates generally to hydrogels and manufacturing methods thereof, and more particularly to a pH-responsive hydrogel for decreasing the nutrient absorption in the small intestine and manufacturing method thereof.

Background

Metabolic syndrome is a common disorder and closely related to several comorbidities, such as type II diabetes, nonalcoholic fatty liver disease (NAFLD) and cardiovascular disease. Excess nutrition uptake can lead to obesity, impaired glucose response, and dyslipidemia, which are generally termed under the umbrella of metabolic syndrome. As the chief location for digestion and absorption, the intestine plays a leading role in the nutrient uptake. Therefore, regulating the absorption of intestinal tract may be one of effective ways to treat metabolic syndrome. For example, Xenical efficiently inhibits lipase and further blocks the lipid uptake in body. However, Xenical can also cause side effects such as steatorrhea, frequent bowel movements, and interfering with the absorption of fat-soluble vitamins.

Gastric bypass, also called Roux-en-Y gastric bypass, is a type of weight-loss surgery that involves creating a small pouch from the stomach and connecting the newly created pouch directly to the small intestine. After gastric bypass, swallowed food will go into this small pouch of stomach and then directly into the small intestine, thereby bypassing most of the stomach and the first section of the small intestine. However, this invasive surgery is only recommended for severely obese patients, and only about 1% of eligible patients are willing to undergo this surgery.

A less invasive procedure "Endobarrier" was first proposed in 2007 and introduced into clinical research. It is an endoscopically implanted device anchored in the upper part of the proximal duodenum. The duodenojejunal polymer sleeve would act as a physical barrier to prevent contact between the ingested food and the intestinal mucosa. Though helpful in achieving improvements in metabolic parameters, EndoBarrier requires annual removal, and numerous side effects, such as nausea, gastrointestinal bleeding, and even device migration have been reported. Thus, we aim to design an edible and biodegradable supplement forming a temporary barrier on the gastrointestinal tract to reduce immoderate absorption. The barrier mimics the bypassing effect of Roux-en-Y surgery and EndoBarrier, without having patients undergo invasive procedures.

Sucralfate is an FDA-approved, orally administered polymer consisting of sucrose octasulfate and polyaluminum complex. It has high affinity for mucosa in acidic environment, inactivates pepsin, and adsorbs bile salts. Sucralfate is often used to treat gastric ulcer, gastritis, gastroesophageal reflux. However, the daily dosage of sucralfate to achieve glycemic control would be costly.

To address this issue, we seek to reduce the amount of sucralfate required while enhancing the barrier properties to provide a safe and effective treatment for metabolic syndrome and associated complications.

SUMMARY OF INVENTION

Disclosed herein is related to an edible and biodegradable supplements, comprising: a pH-responsive hydrogel can form a transient covering on gastrointestinal tract as a temporary barrier to prevent excessive absorption. A methods of manufacturing the hydrogel, comprising the steps of: Mixing an aqueous solution of pectin and an acid-treated sucralfate to obtain a pH-responsive hydrogel, the aluminum ions release from sucralfate in acidic environment serve as a crosslink reagent to interact with pectin, wherein the sucralfate can abbreviate to aluminum sucrose octasulfate, Pectin Sucralfate Hydrogel can abbreviate to PSH.

In some embodiments, the invention provides a pH-responsive hydrogel, which is mixing by an aqueous solution of pectin and hydrogen chloride-treated sucralfate.

In some embodiments, the pectin is selected from a group consisted of polyacrylic acid, carboxymethyl cellulose, fucoidan, carbomer, xanthan gum, carrageenan, gellan gum, guar gum, gelatin, collagen and anionic gelling polymer.

In some embodiments, the acid for treated sucralfate is selected from a group consisted of hydroiodic acid, hydrobromic acid, sulfuric acid, nitric acid, hydrosulfuric acid, hydrofluoric acid, phosphoric acid, boric acid, formic acid, acetic acid, carbonic acid, critic acid and the organic, mineral acid under pH 7.

In some embodiments, the aluminum hydroxide species of sucralfate is selected from a group consisted of iron (III) hydroxide, calcium hydroxide, magnesium hydroxide, and multivalent cationic hydroxide.

In some embodiments, the sucrose-sulfate component of sucralfate is selected from a group consisting of dextran sulfate, dextrin, amylopectin sulfate, amylose, cellulose sulfate, carrageenan, chondroitin sulfate, glucosamine sulfate, heparin, heparan sulfate, raffinose sulfate.

In some embodiments, the method for manufacturing pH-responsive hydrogel, comprising the steps of:
(1) replacing pectin by anionic gelling polymer;
(2) treating sucralfate with the organic, mineral acid under pH 7;
(3) replacing the aluminum hydroxide species of sucralfate by multivalent cationic hydroxide;
(4) replacing the sucrose-sulfate component of sucralfate by dextran sulfate, dextrin, amylopectin sulfate, amylose, cellulose sulfate, carrageenan, chondroitin sulfate, glucosamine sulfate, heparin, heparan sulfate, raffinose sulfate.

In some embodiments, the pH-responsive hydrogel has the characteristic of mucosal adhesion.

In some embodiments, the pH-responsive hydrogel has various viscosity in different gastrointestinal pH.

In some embodiments, the pH-responsive hydrogel is used for decreasing the absorption of nutrients in gastrointestinal system by forming physical barrier between gastrointestinal tract and food.

In some embodiments, the viscosity of hydrogel is reversible between pH value 0.8 to 9. The viscosity of hydrogel in duodenum is higher than in small intestine, the viscosity of hydrogel in small intestine is higher than stomach.

In some embodiments, the pH-responsive hydrogel is used for forming the physical barrier between gastrointestinal tract and food, the intensity of physical barrier in small intestine is higher than duodenum, the intensity of physical barrier in duodenum is higher than stomach.

In some embodiments, the concentration of hydrogen chloride is between 0.1 N to 0.5 N.

In one embodiment, the pH value of pH-responsive hydrogel is 1.2. In this embodiment, the pH-responsive hydrogel is composed of the citrus pectin 1%; the acid-treated sucralfate 0.1%, which comprising: the galacturonic acid >74%; the methoxy group >6.7%.

In some embodiments, the method for manufacturing a pH-responsive hydrogel, comprising:
(1) dissolving the pectin with water to obtain an aqueous solution of pectin;
(2) treating sucralfate with hydrogen chloride to obtain an acid-treated sucralfate;
(3) mixing the aqueous solution of pectin and the acid-treated sucralfate to obtain the pH-responsive hydrogel.

The present invention relates to the pH-responsive hydrogel, which is different from health supplements or weight-loss drugs. The pH-responsive hydrogel is used for forming the physical barrier to decrease the nutrients uptake in small intestine. The properties of the hydrogel, including viscosity, adhesion and blocking effect can be varied depending on pH-value of gastrointestinal tract. The present invention imitates the treatment effect of metabolic syndrome associated disorders after gastric and intestinal bypass surgeries; it is used as oral administration to achieve the efficacy instead of invasive surgery.

The present invention relates to the pH-responsive hydrogel, the hydrogel can block the absorption of glucose and decrease the elevation of blood glucose level in vivo. Also, the hydrogel can decrease weight gain, accumulation of low-density lipoprotein and hepatic lipid deposition in vivo. The manufacturing method of the said hydrogel, which is provided by present invention, possesses at least the following advantages: (i) the material is easy to obtain; (ii) no requirement of expensive equipment in whole process; (iii) it takes only 2 hours and low cost (iv) without cytotoxicity. The hydrogel provided by the present invention can be administered to a subject suffering from slightly obesity, overweight, metabolic syndrome, or diabetes. The viscosity of the hydrogel barrier can be adjusted to satisfy the needs of various patients by tuning the ratio of the components in the composition.

DETAILED DESCRIPTION OF THE INVENTION

Figure 1A:
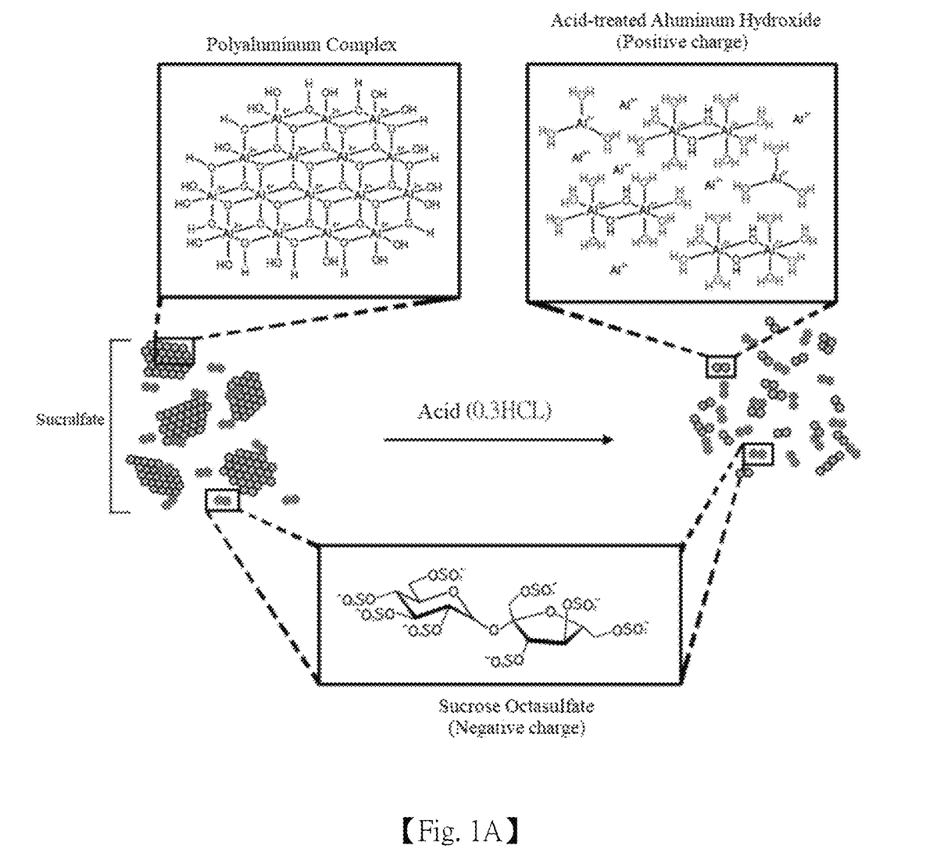
FIG. 1A is a schematic of an acid-treated sucralfate of the invention, showing the sucralfate is treated with acid to transform into the acid-treated sucralfate.

In some embodiments, the pH-responsive hydrogel can increase the secretion of mucoprotein, inhibit the protease activity and protect the cell. The FIG. 1A shows the synthesize illustration of acid-treated sucralfate.

Figure 1B:
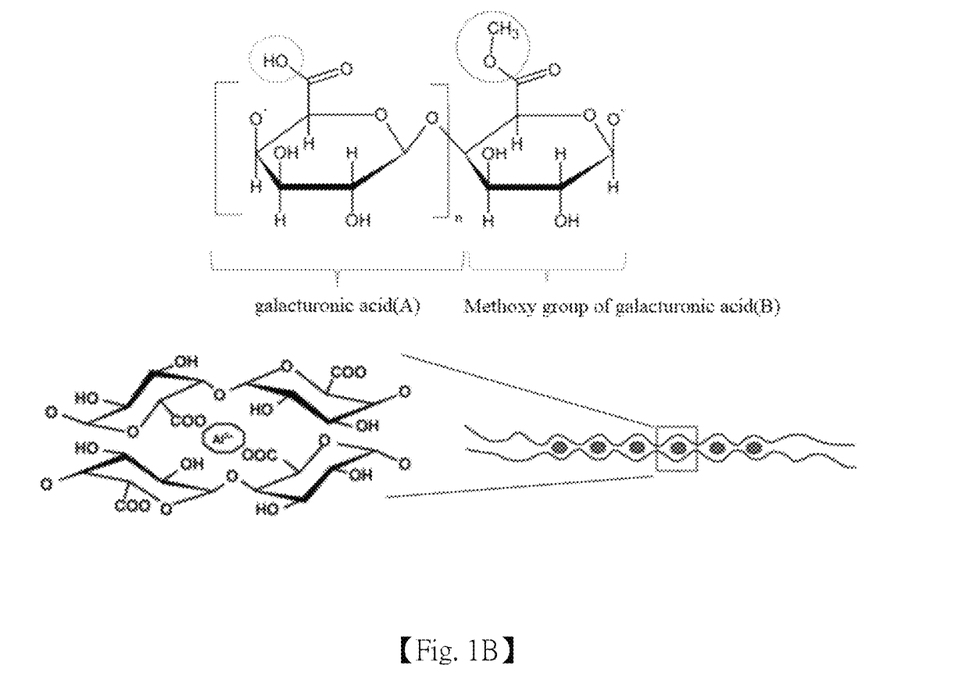
FIG. 1B depicts the chemical structure of citrus pectin.

In some embodiments, the pectin is obtained from a citrus. The citrus pectin not only forms the hydrogel with multivalent cations, but is proved to possess the benefit to maintain the mucus integrity, and increase the number of Bacteroidota. The FIG. 1B shows the structure of citrus pectin.

Figure 1C:
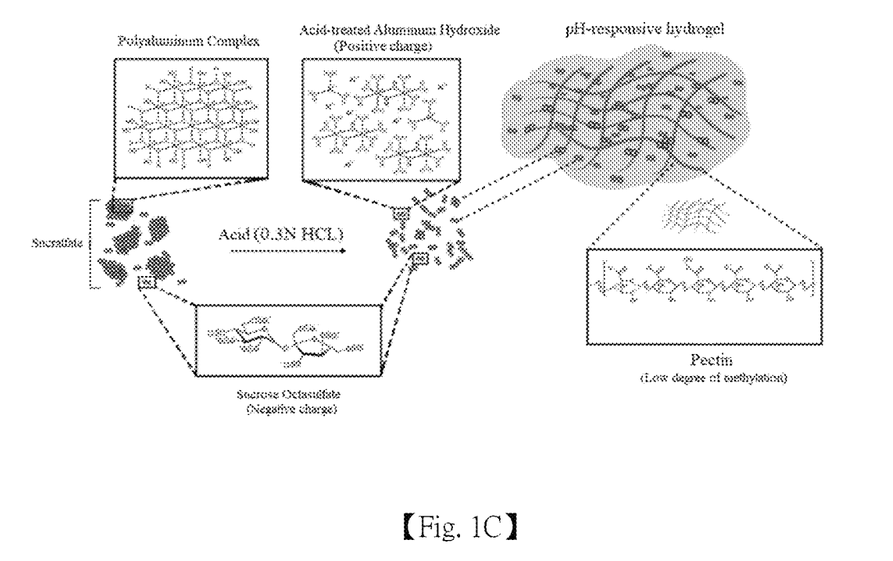
FIG. 1C is a schematic of a pH-responsive hydrogel, showing the pH-responsive hydrogel is composed of acid-treated sucralfate and pectin.

As shown in FIG. 1C, the hydrogel provided herein generally comprises:
an aqueous solution of pectin which is obtained from dissolving pectin with water;
an acid-treated sucralfate which is obtained from treating hydrogen chloride with sucralfate; and
a pH-responsive hydrogel which is obtained by mixing the aqueous solution of pectin with acid-treated sucralfate; wherein the pH-responsive hydrogel can response to various pH environment and showed different viscosity, the hydrogel provides the physical barrier between gastrointestinal and food to decrease the uptake of nutrients. Using the electrostatic interaction between pectin and aluminum ions of sucralfate to synthesized pH-responsive hydrogel. The dynamic viscosity and barrier effect of the pH-responsiveness relies on the number of cations release from hydroxide species in different environment, providing reversible shifting from a hydrogel to a complex coacervate system.

Figure 2:
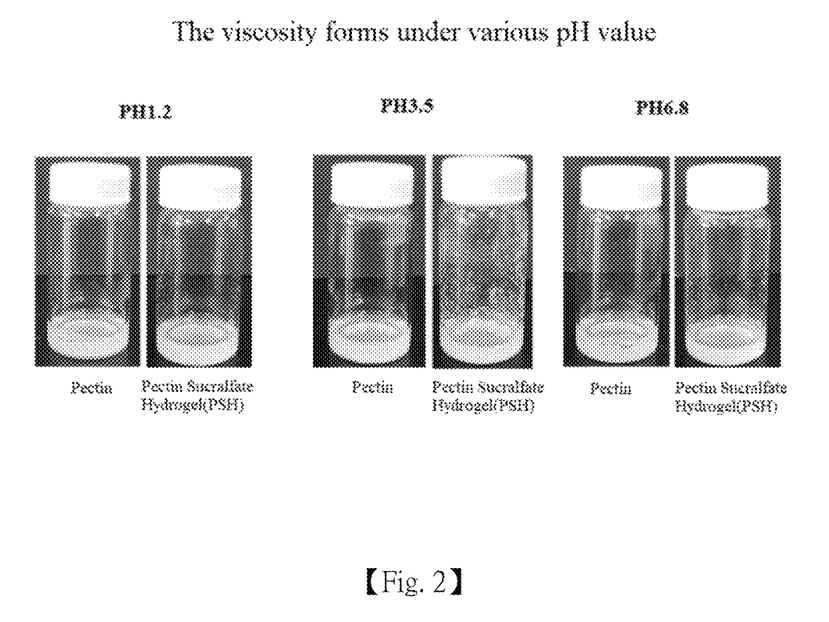
FIG. 2 is an illustration of the viscosity forms of pectin and PSH in different pH environment.

As shown in FIG. 2, the hydrogel provided herein has different viscosity forms in different gastrointestinal pH (stomach, pH 1.2; duodenum, pH 3.5; intestine, pH6.8). The FIG. 2 represent the viscosity forms of PSH group and pectin group at different part of gastrointestinal.

Figure 3:
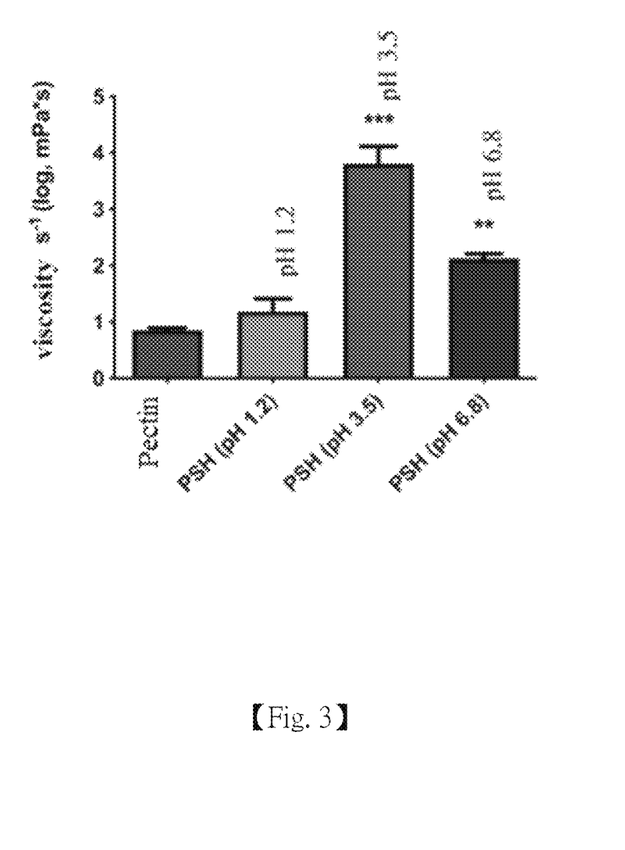
FIG. 3 is a graph comparing the viscosity value of pectin and PSH in different gastrointestinal pH.

As shown in FIG. 3, the viscosity value of pectin group and the viscosity value of PSH group in different gastrointestinal pH (stomach, pH 1.2, duodenum: pH3.5, intestine: pH6.8). (One-way ANOVA with multiple comparison tests was adopted for the statistical difference of the experiment, n=3 per arm, $P<0.002$, *$P<0.0001$)

Example 1: The Functional Barrier Test In-Vitro

Figure 4:
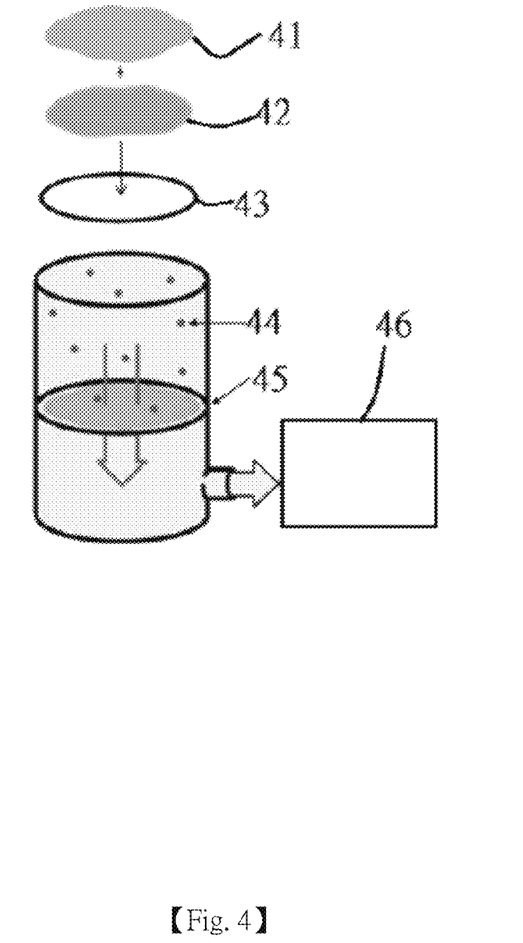
FIG. 4 is a schematic of the barrier function test, the pH-responsive hydrogel was applied on a mucin-coated cellulose membrane and mounted onto a microfiltration laboratory apparatus, and the glucose permeation was measured by a glucose meter.
Figure 5:
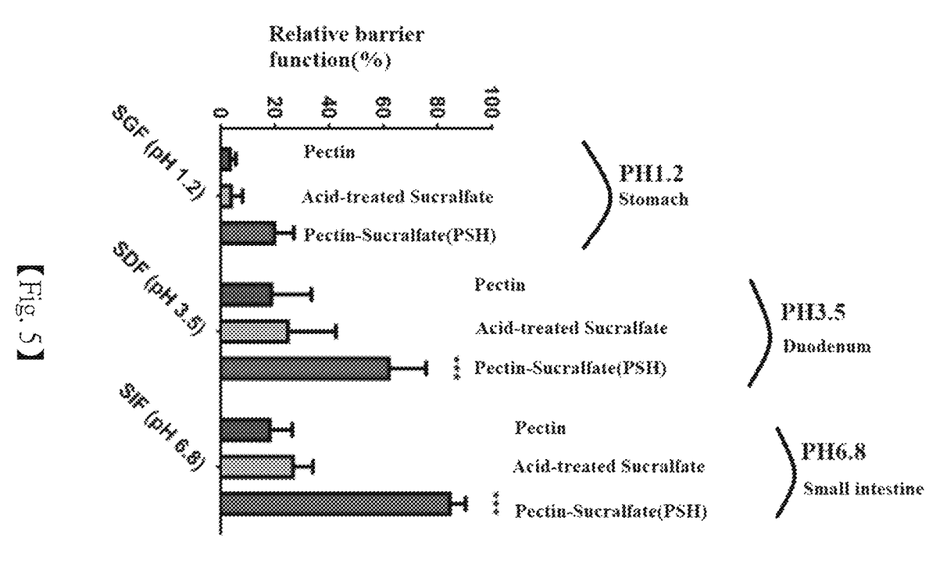
FIG. 5 is a graph comparing the relative barrier function of pectin, acid-treated sucralfate, PSH tested with glucose solution in different gastrointestinal pH.

As shown in FIG. 4, the barrier properties of pH-responsive hydrogel were tested by permeability test, the hydrogel was coated on mucin-coated cellulose membrane, followed by using the 500 mg dL-1 glucose solution to evaluate the relative barrier effect of pectin, acid-treated sucralfate and PSH in different pH environment (stomach, pH 1.2, duodenum, pH 3.5; intestine, pH 6.8). As shown in FIG. 5. The Pectin Sucralfate Hydrogel (PSH) shows remarkably enhanced and greater barrier function in simulated duodenal and intestinal environments (two-way ANOVA with multiple comparison tests was adopted for the statistical difference of the experiment, n=3 per arm, ***$P<0.0001$ compared to pectin). The symbol of FIG. 4. Coating material 41, mucin 42, Cellulose membrane 43, Glucose solution 44, Coated membrane 45, Glucose meter 46.

Example 2: The Mucoadhesive Test In Vivo

Figure 6:
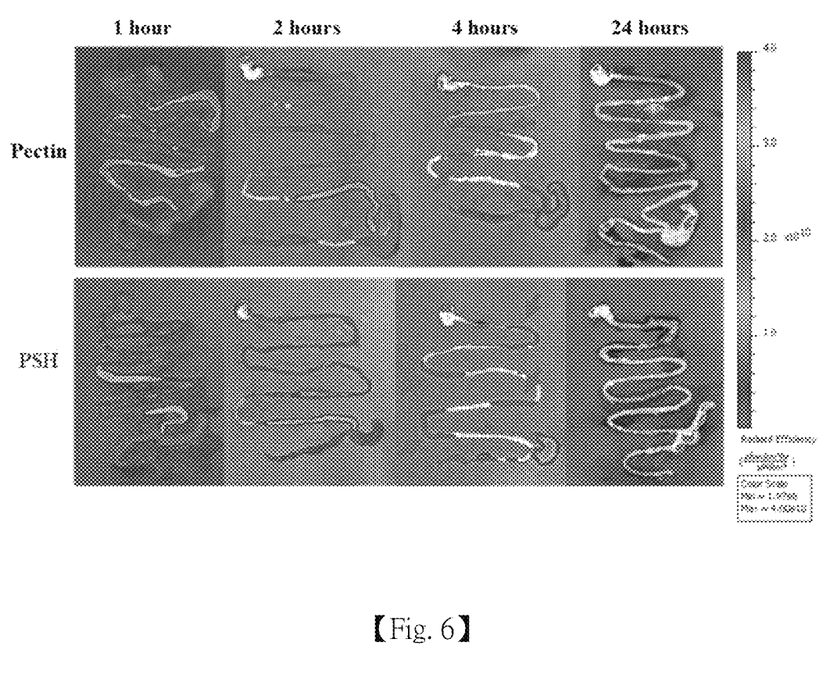
FIG. 6 is a fluorescence image of in vivo mucus adhesion evaluation.

Mice were gavaged with hydrogel (250 mg per kg mouse) encapsulated with fluorescence albumin, the gastrointestinal tracts from the stomach to the colon were harvested in 1, 2, 4, 24 hours and placed in 3D in-vivo imaging system (IVIS) to imaged. As shown in FIG. 6. After 4 hours, the fluorescence intensity of pectin group is less than PSH group. FIG. 6. shows that pectin sucralfate hydrogel can attach on GI tract for a longer period. Also, the pectin and PSH can be exiled from the gastrointestinal tract within 24 hours. The FIG. 6 shows the mucoadhesive of PSH and pectin in vivo. Fluorescein isothiocyanate is the common dye to label protein.

Example 3: The Functional Barrier Test In Vivo

Figure 7:
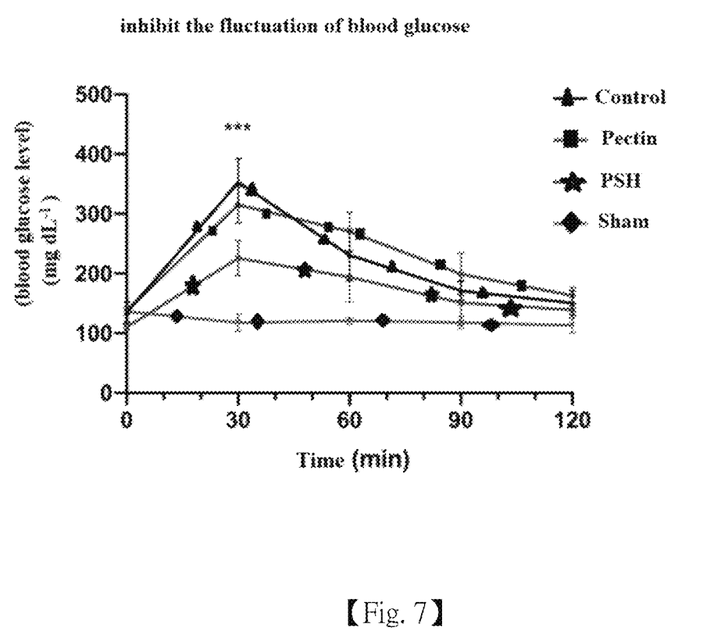
FIG. 7 is a graph comparing the oral glucose tolerance test (OGTT) curves.
Figure 8:
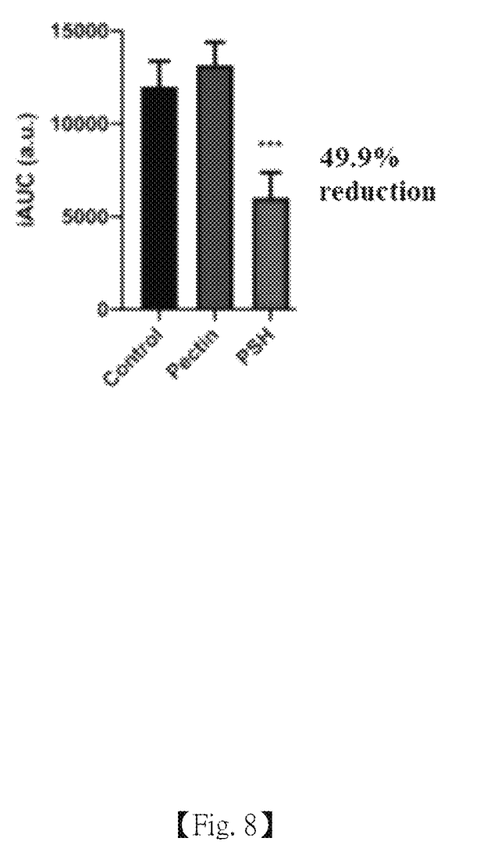
FIG. 8 is a graph comparing the incremental area under curve of OGTT.

To assess the barrier function of hydrogel on nutrient absorption in vivo, the glucose tolerance test was performed. Mice were gavaged with hydrogel and left for 1 hour for the hydrogel to attach on the mucous layer of the small intestine, then the glucose solution were fed to mice and blood glucose levels were tested at different timepoint to plot the curve of blood glucose. As shown in FIG. 8. The PSH group shows reduction in blood glucose response, with a 49.9% reduction in iAUC compared to control group (one-way ANOVA with multiple comparison tests was adopted for the statistical difference of the experiment, n=4 per arm, ***P<0.0001). The PSH can block most of glucose uptake by forming the physical barrier. The oral glucose tolerance test (OGTT), also known as the glucose tolerance test, measures the body's response to sugar (glucose). The glucose tolerance test can be used to screen for dysregulate of glucose and diabetes. As shown in FIG. 7. In oral glucose tolerance test, the blood glucose level (mg Dl-1) of PSH group compared to pectin group and control group indicate the fluctuations of blood glucose were inhibited by the physical barrier formed by PSH. As shown in FIG. 8. Incremental blood glucose area-under-curve (iAUC) and area under the curve (AUC) are widely used to diagnose impaired fasting glucose (IGT) of oral glucose tolerance test (OGTT). iAUC for evaluated the blood glucose level in OGTT can be processed by using trapezoidal rule, trapezoidal method, and compound trapezoidal formula. Typically, AUC can be obtained by trapezoidal rule.

Example 4: Long-Term Therapeutic Effect of pH-Responsive Hydrogel In Vivo

Figure 9:
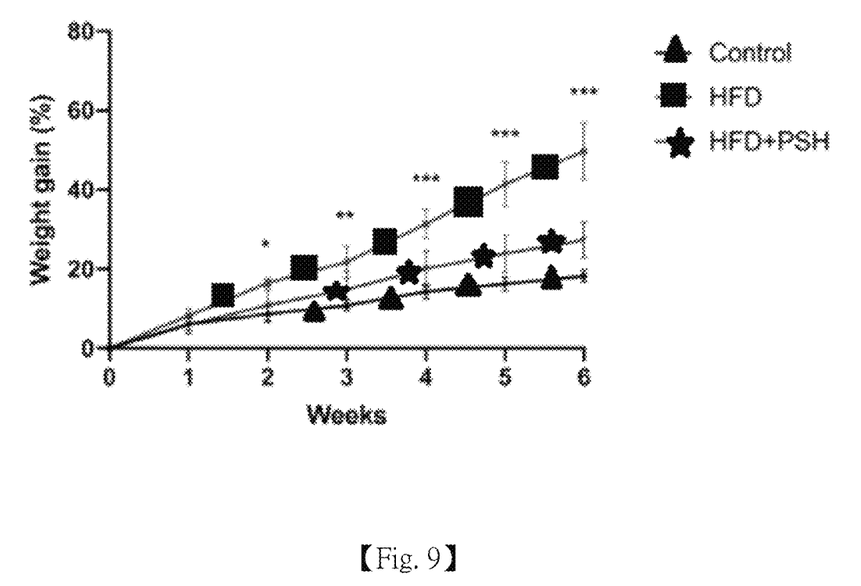
FIG. 9 is a graph comparing the weight gain (%) of mice after feeding the high fat diet and HFD+PSH.
Figure 10:
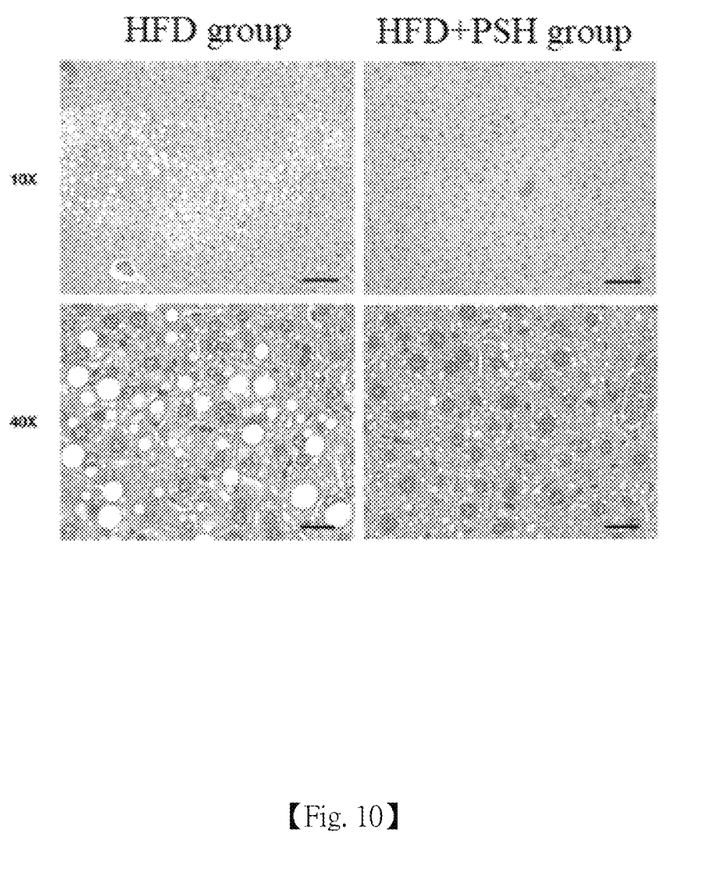
FIG. 10 is a histological analysis illustration of hepatic fat accumulation, showing the PSH can decreases hepatic fat deposition despite feeding HFD.
Figure 11:
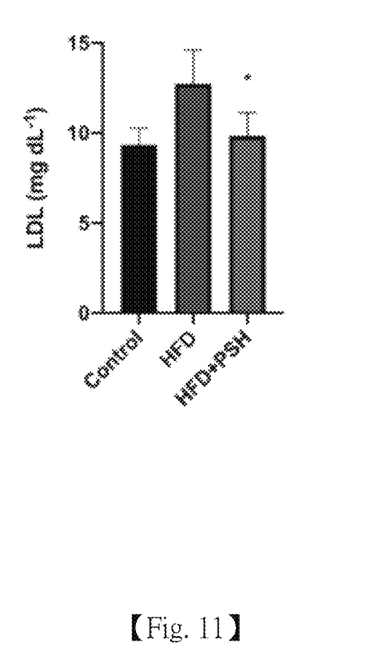
FIG. 11 is a graph of comparing the serum low-density lipoprotein level with control group, HFD group, HFD+PSH group, showing the HFD+PSH group decrease the LDL level.

To observe the therapeutic effect of PSH on metabolic syndrome, the mice were fed High Fat Diet (HFD) to establish an obesity model. PSH was oral administered (125 per kg) daily for 6 weeks to investigate its effects on metabolic parameter. As shown in FIG. 9, weight gain is lower in the HFD+PSH group compared to the HFD group, eventually leading to a 28% decrease in weight gain after 6 weeks which shows the long-term weight loss effect of the hydrogel (two-way ANOVA with multiple comparison tests was adopted for the statistical difference of the experiment, n=6, ***P<0.0001). In the HFD-induced obesity model, the PSH group has the long-term effect of decreased the weight gain, response to glucose, accumulation of body fat. Therefore, the barrier generated by PSH can inhibit the HFD absorption. ANOVA test is a type of statistical test used to determine if there is a statistically significant difference between two or more categorical groups by testing for differences of means using variance. FIG. 10 is the histological analysis of the liver section under 10x, 40x views. As shown in FIG. 10, the HFD+PSH group can reduce the lipid deposition in liver. FIG. 11 shows the HFD+PSH group can significantly decrease the low-density lipoprotein cholesterol (LDL) levels compared to HFD group. LDL stands for low-density lipoproteins. It is sometimes called the "bad" cholesterol, the main function of LDL was delivered the cholesterol to whole body. The lipids need to be attached to the proteins so they can move through the blood. Have a high LDL level, this means extra LDL along with other substances, forms plaque in blood vessels. The plaque builds up in arteries can caused atherosclerosis or coronary artery disease. PSH can apply to decrease the number of LDL, which carries cholesterol.

As shown in FIG. 3, the present invention relates to the pH-responsive hydrogel, the viscosity of hydrogel is reversible in pH value between 0.8 to 9, the viscosity of hydrogel in duodenum (pH3.5) is higher than intestine (pH6.8), the viscosity of hydrogel in intestine (pH6.8) is higher than stomach (pH1.2).

As shown in FIG. 5. The present invention relates to the pH-responsive hydrogel, the hydrogel is used for forming physical barrier between gastrointestinal digest system and food, the barrier intensity of hydrogel in intestine (pH6.8) is higher than duodenum (pH 3.5), the barrier intensity of hydrogel in duodenum (pH3.5) is higher than stomach (pH 1.2). In the gastric environment, despite the presence of aluminum ions, the pectin does not have insufficient deprotonation of the carboxyl group to develop into a hydrogel. In the duodenal environment, the negative carboxyl groups bind to the positive aluminum ion to convert into a hydrogel. The viscosity value of PSH peaks at pH value 4 to 5 and gradually decreases as the aluminum ion are hydroxylated into aluminum mono-hydroxide, which may be structurally too large to be retained in the hydrogel structure. Finally, the oppositely charged polyelectrolytes transform into a complex coacervate system in intestinal environment.

The present invention relates to a pH-responsive hydrogel, the hydrogel provides herein is used for metabolic syndrome, diabetes, obesity, overweight patient. The pH-responsive hydrogel is administered before meal to lower the immediate glucose response by forming the coating layer on gastrointestinal and inhibit the overabsorption of nutrients.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A pH-responsive hydrogel comprising:
a pectin solution; and
an acid-treated metal salt of sulfated carbohydrate.
2. The hydrogel of claim 1, wherein the pectin solution comprises polyacrylic acid, carboxymethyl cellulose, fucoidan, carbomer, xanthan gum, carrageenan, gellan gum, guar gum, gelatin, collagen, or anionic gelling polymer.
3. The hydrogel of claim 1, wherein the acid is selected from the group consisting of hydrochloric acid, hydriodic acid, hydrobromic acid, sulfuric acid, nitric acid, hydrosul- furic acid, hydrofluoric acid, phosphoric acid, boric acid, formic acid, acetic acid, carbonic acid, and critic acid.

4. The hydrogel of claim 1, wherein the metal salt of sulfated carbohydrate comprises a hydroxide of metal cation.

5. The hydrogel of claim 4, wherein the hydroxide of metal cation is selected from the group consisting of aluminum hydroxide, iron hydroxide, calcium hydroxide, and magnesium hydroxide.

6. The hydrogel of claim 1, wherein the sulfated carbohydrate is selected from the group consisting of dextran sulfate, dextrin, amylopectin sulfate, amylose, cellulose sulfate, carrageenan, chondroitin sulfate, glucosamine sulfate, heparin, heparan sulfate, and raffinose sulfate.

7. The hydrogel of claim 1, which has the characteristics of mucoadhesive.

8. The hydrogel of claim 1, which has various viscosity in the different part of gastrointestinal with various pH value.

9. The hydrogel of claim 1, which is used for forming the physical barrier between gastrointestinal tract and food to decrease the nutrient uptake of gastrointestinal tract.

10. The hydrogel of claim 1, wherein the viscosity of the hydrogel is reversible between pH value 0.8 to 9.

11. The hydrogel of claim 1, wherein the viscosity of the hydrogel in duodenum is higher than small intestine, and the viscosity of the hydrogel in small intestine is higher than stomach.

12. The hydrogel of claim 1, wherein the barrier intensity of hydrogel in small intestine is higher than duodenum, the barrier intensity of hydrogel in duodenum is higher than stomach.

13. The hydrogel of claim 1, wherein the concentration of the acid is 0.1 N to 0.5 N.

14. The hydrogel of claim 1, comprising:
1% pectin; and
0.1% acid-treated sucralfate;
wherein the sucralfate comprises >74% of galacturonic acid and >6.7% of methoxy group.

15. A method for manufacturing a pH-responsive hydrogel, comprising steps of:
a) dissolving a pectin to obtain a pectin solution;
b) treating metal salt of sulfated carbohydrate with acid to obtain an acid-treated metal salt of sulfated carbohydrate; and
c) mixing the pectin solution with acid-treated metal salt of sulfated carbohydrate to obtain the pH-responsive hydrogel.

* * * * *